United States Patent [19]

Sugihara et al.

[11] Patent Number: 4,928,513
[45] Date of Patent: May 29, 1990

[54] SENSOR

[75] Inventors: Takashi Sugihara, Nara; Kazutaka Uda, Tenri; Hiroki Tabuchi; Yasuhiko Inami, both of Nara; Masaya Hijikigawa, Yamatokoriyama; Shoei Kataoka, Tanashi, all of Japan

[73] Assignee: Sharp Kabushiki Kaisha, Osaka, Japan

[21] Appl. No.: 78,741

[22] Filed: Jul. 28, 1987

[30] Foreign Application Priority Data

| Jul. 29, 1986 | [JP] | Japan | 61-179625 |
| Apr. 22, 1987 | [JP] | Japan | 62-99323 |
| May 21, 1987 | [JP] | Japan | 62-126164 |
| May 27, 1987 | [JP] | Japan | 62-130607 |
| Jun. 8, 1987 | [JP] | Japan | 62-143496 |

[51] Int. Cl.$^5$ .................................. G01N 27/04
[52] U.S. Cl. .................................. 73/1 G; 73/23; 73/335; 73/29; 338/34; 338/35
[58] Field of Search ............... 73/335, 1 G, 23, 27 R, 73/29; 338/34, 35

[56] References Cited

U.S. PATENT DOCUMENTS

| 4,177,667 | 12/1979 | Rolf et al. | 73/1 G |
| 4,337,658 | 7/1982 | Motchenbacher et al. | 73/335 |
| 4,343,768 | 8/1982 | Kimura | 422/97 |
| 4,381,922 | 3/1983 | Frey et al. | 73/23 |
| 4,497,701 | 2/1985 | Murata et al. | 73/335 X |
| 4,561,286 | 12/1985 | Seikler et al. | 73/23 |
| 4,580,439 | 4/1986 | Manaka | 73/23 |
| 4,635,467 | 1/1987 | Hoffa et al. | 73/1 G |

FOREIGN PATENT DOCUMENTS

| 0009252 | 4/1980 | European Pat. Off. |
| 0021225 | 1/1981 | European Pat. Off. |
| 0137687 | 4/1985 | European Pat. Off. |
| 900663 | 7/1962 | United Kingdom |
| 11135097 | 11/1968 | United Kingdom |
| 2172999A | 10/1986 | United Kingdom |
| 12183344A | 6/1987 | United Kingdom |

Primary Examiner—Tom Noland
Attorney, Agent, or Firm—Irell & Manella

[57] ABSTRACT

A sensor having a pair of sensor units, one of which is a detecting sensor unit and the other of which is a reference sensor unit, wherein each of the units comprises a substrate with a hollow portion, a thin insulating layer with a bridge, cantilever or diaphragm shape disposed on the substrate, a sensitive film disposed on the bridge, cantilever or diaphragm portion of the thin insulating layer, and a pair of electrodes being in contact with the sensitive film, the sensitive film section of the detecting sensor unit being exposed to an atmosphere to be measured so that the electrical resistance of the sensitive film changes with a variation in the physical quantity of the atmosphere to be detected, and the sensitive film section of the reference sensor unit being sealed within a shielding container so that the electrical resistance of the sensitive film is not influenced by a variation in the physical quantity of the atmosphere outside of the container, whereby the absolute physical quantity of the atmosphere to be detected is determined by the output power of the sensor based on a difference between the electrical resistance of the detecting sensor unit and the electrical resistance of the reference sensor unit.

23 Claims, 8 Drawing Sheets

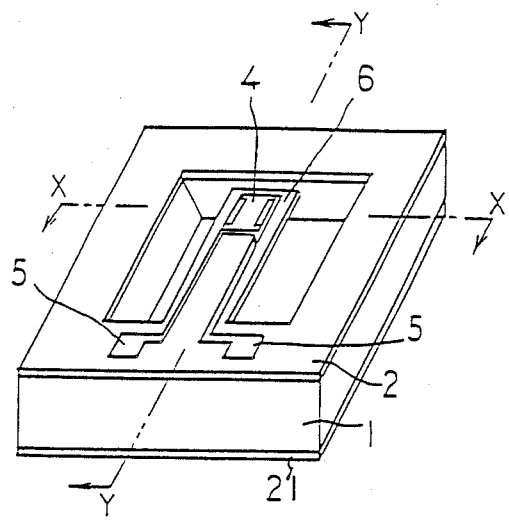
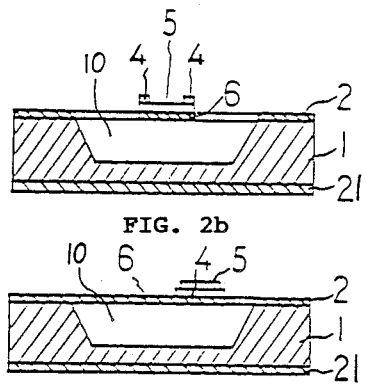
FIG. 2b
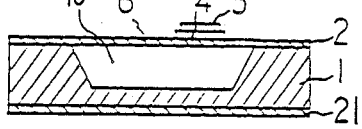
FIG. 2c
FIG. 2a
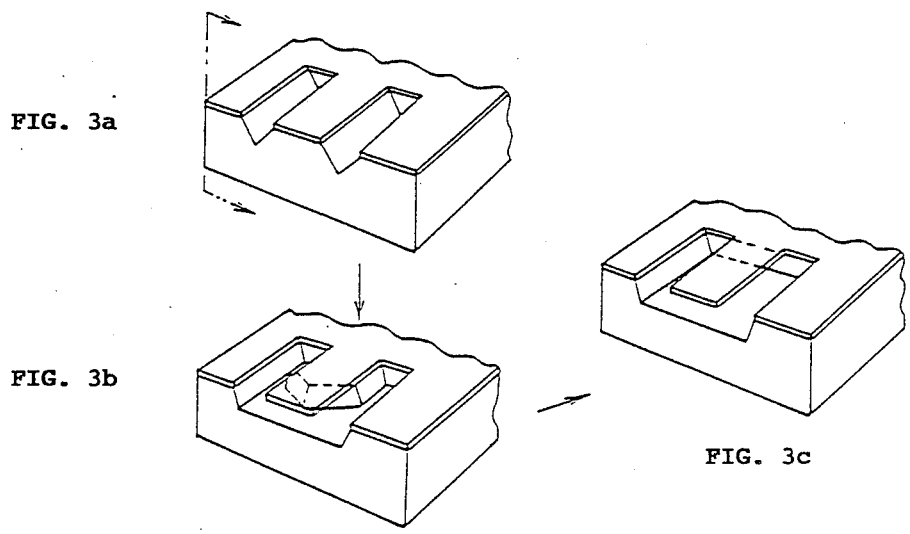
FIG. 3a
FIG. 3b
FIG. 3c

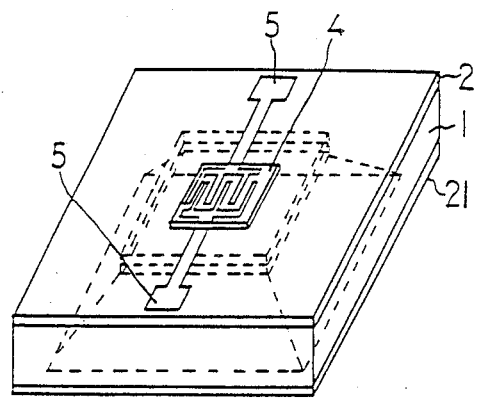
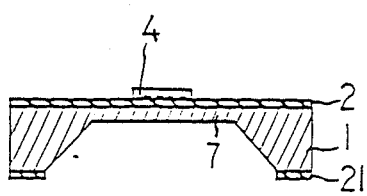
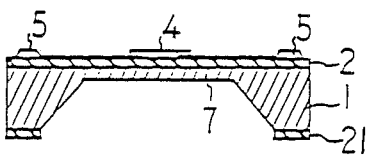
FIG. 5a
FIG. 5b
FIG. 5c
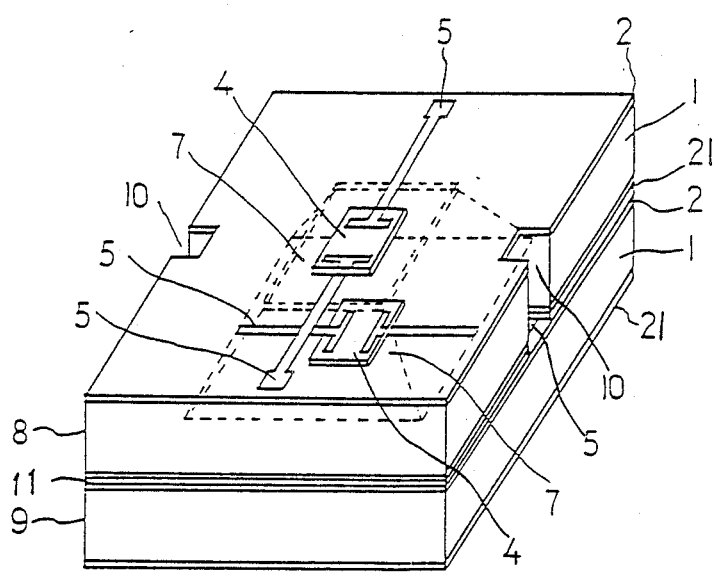
FIG. 6

SENSOR

BACKGROUND OF THE INVENTION

1. Field of the invention

This invention relates to a sensor having a pair of sensor units, one of which is a detecting unit and the other of which is a reference unit. More particularly, it relates to a moisture, gas or infrared ray sensor having excellent detection ability due to its high sensitivity, excellent response characteristics and lowered power consumption.

2. Description of the prior art

A variety of moisture sensors have been developed. Particularly, sensors for detecting relative humidity in the atmosphere utilize the phenomenon that the electrical resistance or the electrical capacity of a moisture sensitive material varies depending upon a variation in the humidity or water vapor of the atmosphere. As moisture sensitive materials, there have been, for example, a moisture sensitive material having a sintered body of metal oxides such as iron oxide ($Fe_2O_3$ or $Fe_3O_4$), tin oxide ($SnO_2$), etc., or a metal oxide film; a moisture sensitive material having a hydrophilic polymer film or a polyelectrolyte; a moisture sensitive material having an electrolyte salt such as lithium chloride (LiCl); and a moisture sensitive material having a hygroscopic resin or polymer film in which conductive particles or fibers such as carbon are dispersed. However, the above-mentioned sensors have difficulties in detecting a slight variation in water vapor of the atmosphere such as that in an operating microwave oven under severe conditions in which the temperature of the atmosphere drastically changes. The reasons are as follows: Provided that the amount of water vapor of the atmosphere to be detected is maintained at a fixed level, when the temperature alone of the atmosphere rises, the relative humidity of the atmosphere is lowered in relation to the saturated water vapor pressure. Moreover, when the temperature of the atmosphere drastically rises, even though a slight increase in water vapor arises, an increase in the relative humidity of the atmosphere is offset by the change in temperature, or a decrease in the relative humidity is affected. As a result, substantial variation in water vapor cannot detected. Therefore, for the detection of humidity of certain environments, the detection of absolute humidity (i.e., an amount of water vapor) is advantageous over that of relative humidity.

As a detecting means for the detection of absolute humidity, there have been apparatuses utilizing the decay of microwaves due to water vapor or absorption of infrared rays due to water vapor. Although these apparatuses are superior in that a slight variation in the amount of water vapor can be detected even under severe conditions where the above-mentioned drastic changes in temperature arise, the structure of such a temperature compensation means becomes unavoidably large and results in a high production cost. On the other hand, there has been a thermal conduction type moisture sensor provided with a pair of thermistors for the detection of absolute humidity utilizing a difference in the thermal conductivity between the wet air and the dry air. This moisture sensor is compact and exhibits a moisture-detecting ability even under severe conditions where drastic changes in temperature arise, but it cannot produce sufficient output power based on a slight variation in the amount of water vapor so that it is inferior in detection sensitivity and response speed.

SUMMARY OF THE INVENTION

The sensor of this invention, which overcomes the above-discussed and numerous other disadvantages and deficiencies of the prior art, has a pair of sensor units, one of which is a detecting sensor unit and the other of which is a reference sensor unit, wherein said detecting sensor unit comprises a substrate with a hollow portion, a thin insulating layer with a bridge, cantilever or diaphragm shape disposed on said substrate, a sensitive film disposed on the bridge, cantilever or diaphragm portion of said thin insulating layer, and a pair of electrodes being in contact with said sensitive film, the sensitive film section being exposed to an atmosphere to be measured so that the electrical resistance of said sensitive film changes with a variation in the physical quantity of said atmosphere to be detected; and said reference sensor unit comprises a substrate having a hollow portion, a thin insulating layer with a bridge, cantilever or diaphragm shape disposed on said substrate, a sensitive film disposed on the bridge, cantilever or diaphragm portion of said thin insulating layer, and a pair of electrodes being in contact with said sensitive film, the sensitive film section being sealed within a shielding container so that the electrical resistance of said sensitive film is not influenced by a variation in the physical quantity of the atmosphere outside of said container, whereby the absolute physical quantity of the atmosphere to be detected is determined by the output power of said sensor based on a difference between said electrical resistance of the detecting sensor unit and said electrical resistance of the reference sensor unit.

In a preferred embodiment, the thickness of said thin insulating layer is 100 $\mu$m or less.

In a preferred embodiment, the sensitive film is made of SiC, TaN, Ge, Si, $BaTiO_3$ or a material mainly containing at least one of these substances.

In a preferred embodiment, the surface of said sensitive film is formed into an irregular pattern. In a more preferred embodiment, the sensitive film is made into a meandering pattern. In a still more preferred embodiment, the surface of said sensitive film is etched into an irregular pattern or the surface of the underlying layer on which said sensitive film is disposed is formed into an irregular pattern, so that the surface of the sensitive film disposed on the irregular pattern surface of said underlying layer can be formed into an irregular pattern.

In a preferred embodiment, the substrate and the container are mainly made of silicon or a compound semiconductor composed of elements of the III-V groups.

In a preferred embodiment, the electrode is made of metal having a thermal conductivity of 100 W/m.K or less. In a more preferred embodiment, the metal is titanium.

In a preferred embodiment, the detecting sensor unit and the reference sensor unit are separate from each other.

In a preferred embodiment, the diaphragm type detecting sensor unit and the diaphragm type reference sensor unit are united into one body by depositing said detecting sensor unit on said reference sensor unit in such a manner that the sensitive film section of said reference sensor unit is sealed within the hollow portion of said detecting sensor unit.

In a preferred embodiment, the substrate of said detecting sensor unit is common to that of said reference sensor unit. In a more preferred embodiment, two or more sensitive films are disposed on said substrate.

In a preferred embodiment, the physical quantity is water vapor, gas or infrared rays.

Thus, the invention described herein makes possible the objects of (1) providing a compact and miniaturized sensor which can be manufactured by batch processes used for conventional semiconductor production or other conventional semiconductor production processes, said batch processes being excellent in mass producability and supplying inexpensive sensors that are interchangeable; (2) providing a sensor which can be used as a thermal conduction type moisture sensor that can directly detect the amount of water vapor and that is superior to conventional moisture sensors for detecting relative humidity in the case that the temperature of the atmosphere to be detected drastically changes; (3) providing a sensor in which a microbridge, cantilever or diaphragm structure is used so that the heat capacity of the sensor can be lowered, and moreover the moisture sensitive films are made of a material having a large thermistor constant such as Ge, SiC, TaN, or the like, thereby achieving a high sensitivity, a quick response and a lowered power consumption in the detection of water vapor; (4) providing a sensor which has, in addition to the above-mentioned bridge, cantilever or diaphragm structure, a sensitive film having the surface thereof with a large heat-radiation area, so that the heat capacity can be efficiently lowered; (5) providing a sensor which attains stable detection regardless of contamination on the surface of the sensor by exterior substances such as oil, dust, etc., since the physical quantity to be measured is detected by a physical process; and (6) providing a sensor which has excellent resistance to light and heat and has a long life span.

BRIEF DESCRIPTION OF THE DRAWINGS

This invention may be better understood and its numerous objects and advantages will become apparent to those skilled in the art by reference to the accompanying drawings as follows:

FIG. 2a is a perspective view showing a cantilever type moisture sensor unit of this invention.

FIGS. 2b and 2c, respectively, are cross sectional views taken on lines X—X and Y—Y of FIG. 2a.

FIGS. 3a to 3c are a schematic diagram showing the progress of an etching of the sensor unit wafer of this invention.

FIG. 5a is a perspective view showing a diaphragm type moisture sensor unit of this invention.

FIGS. 5b and 5c are cross sectional views of the moisture sensor unit of FIG. 5a.

FIG. 6 is a perspective view showing a diaphragm type moisture sensor of this invention, in which a detecting sensor unit and a reference sensor unit is united into one body.

FIGS. 7a and 7b, FIGS. 8a and 8b, and FIG. 9, respectively, are perspective views showing a portion of the sensitive film of the sensor unit shown in FIG. 1a.

FIGS. 11b and 11c, respectively, are cross sectional views taken on lines X—X and Y—Y of FIG. 11a.

FIG. 13b is a cross sectional view taken on line A—A of FIG. 13a.

DESCRIPTION OF THE PREFERRED EMBODIMENTS

Example 1

A sensor of this invention has a pair of sensor units self-heated at a certain temperature, one (a first sensor unit) of which is exposed to the atmosphere to be detected and the other (a second sensor unit) of which is sealed within a shielded container enclosing a certain humidity therein. The thermal conductivity of the atmosphere to be detected varies with changes in the amount of water vapor in the said atmosphere, resulting in a difference in the temperature between the first sensor unit and the second sensor unit. By an output power based on the said temperature difference therebetween, the amount of water vapor of the said atmosphere can be accurately detected without being affected by the temperature of the said atmosphere.

Figure 1A:
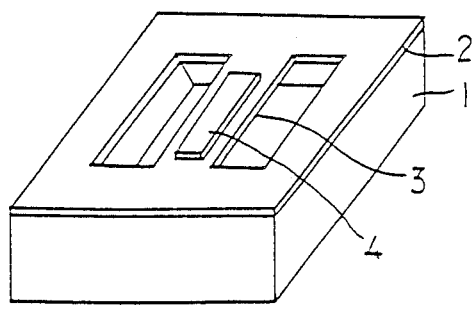
FIGS. 1a and 1b, respectively, are a perspective view and a cross sectional view showing a sensor unit wafer of this invention.
Figure 1B:
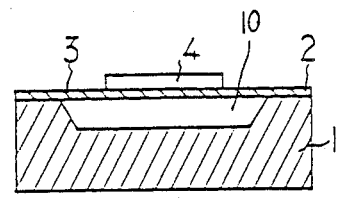
Figure 1C:
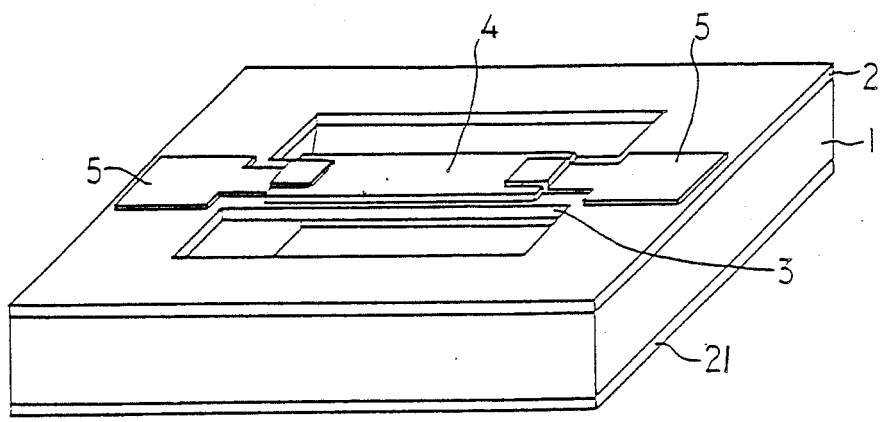
FIGS. 1c and 1d, respectively, are a perspective view and a cross sectional view showing a bridge type moisture sensor unit obtained from the sensor unit wafer of FIGS. 1a and 1b.
Figure 1D:
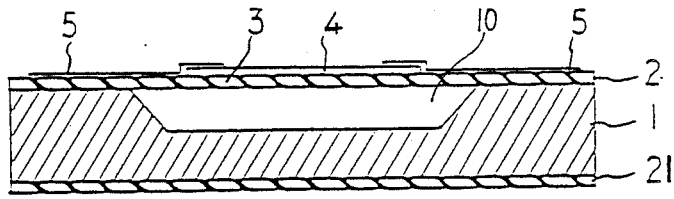

FIGS. 1c and 1d show a moisture sensor unit of this invention, which comprises a Si substrate 1 having a hollow portion 10, a thin insulating layer 2 with a bridge-shaped portion (referred to as a microbridge hereinafter) 3 that is disposed on the substrate 1, a sensitive film 4 disposed on the microbridge 3 and electrodes 5, for detecting electrical resistance of the sensitive film 4, connected to the sensitive film 4. The production process of the microbridge 3 of the sensor unit is as follows: On a Si substrate 1 in which the chemical etching rate varies depending upon the direction of the crystal axis, a thin insulating film 2, a part of which finally forms a microbridge 3 and which functions as a masking substance during an etching treatment of the substrate 1, is disposed by a thermal oxidation technique, vacuum vapor deposition, the sputtering method or chemical vapor deposition, followed by photolithography and a chemical or dry etching technique, resulting in the microbridge 3 of the thin insulating layer 2. In order to mechanically strengthen the microbridge 3, it is useful that the bridge portion is made of both the insulating layer and the Si layer by leaving a Si-substrate portion with the same width as the said bridge portion and with a given thickness on the portion of the back face of the insulating layer 3 corresponding to the microbridge 3. For this purpose, a dopant such as boron is diffused, in advance, into the surface of the Si substrate and the vicinity thereof corresponding to the microbridge 3 at a high concentration, so that the dopant-diffused area works as a shielding layer during anisotropic etching (i.e., a chemical etching). In this way, the microbridge 3 is formed as shown in FIGS. 1a and 1b. Thereafter, the sensitive film 4 and the electrodes 5 are disposed on the microbridge 3. As the insulating-layer material, $SiO_2$, $Si_3N_4$, $Al_2O_2$, etc., which have a low heat capacity and a thermal conductivity that is close to that of the Si substrate may be used. The insulating layer made of the above-mentioned material is preferably set to be 100 μm or less. This insulating layer can be also formed into a cantilever.

Example 2

FIGS. 2a, 2b and 2c show another moisture sensor unit of this invention, which comprises a Si substrate 1 having a hollow portion 10, a thin insulating layer 2 with a cantilever portion 6 extending across the hollow portion 10, a sensitive film 4 disposed on the cantilever portion 6 of the insulating layer 2, and a pair of electrodes 5, for detecting electrical resistance of the sensitive film 4, connected to the sensitive film 4. Each of the electrodes 5 can be formed into a rectangular shape, a comb shape, a wavy pattern or the like. The cantilever portion 6 can be a double-layered structure that is composed of the insulating layer 2 and the Si substrate portion in the same way as the microbridge of Example 1.

The sensitive film 4 is formed on the microbridge 3 or the cantilever portion 6 by vacuum vapor deposition, chemical vapor deposition or the like, followed by a photolithographic process and an etching technique to form the desired fine pattern therein. The area of the thin insulating layer 2 on which the sensitive film 4 is disposed can be of a diaphragm structure other than the bridge or cantilever structure.

Then, thin metal film electrodes 5 are formed on the sensitive film 4 by vacuum vapor deposition, the sputtering method, chemical vapor deposition or the like. Alternatively, the electrodes 5 can be disposed on the insulating layer 2, first, and then the sensitive film 4 is formed on the insulating layer 2 including the electrodes 5 so that it comes into contact with the said electrodes 5. In this case, the surface area of the sensitive film 4 which comes into contact with the atmosphere is not reduced by the electrodes 5, so that the detection of water vapor can be carried out with high sensitivity. As a sensitive film material, Ge, SiC, TaN, Si, $BaTiO_3$, etc., which have a large thermistor constant, can be used. In this example, Ge is used for the sensitive film 4. The electrodes 5 are not necessarily disposed so as to face each other on one surface of the sensitive film 4, but they can be disposed so as to sandwich the sensitive film 4 therebetween when the specific electric resistance of the sensitive film 4 is within a certain range. The thin insulating layer 21 covering the bottom face of the Si substrate 1 functions to prevent the said bottom face from being etched. The said faces of the Si substrate 1 are also covered by a thin insulating layer for the same purpose.

Thereafter, the Si substrate is subjected to an anisotropic etching treatment with an etchant such as a solution containing ethylenediamine, pyrocatechol and water, and the etching of the Si crystal proceeds in the direction of the preferential crystal axis in the area of the Si substrate 1 which is not coated with the insulating layer, so that removal of the portion of the Si substrate positioned below the bridged pattern of the insulating layer 2 can be achieved, as shown in FIGS. 3a to 3c, resulting in a chip of moisture sensor units with a microbridge structure.

A sensor of this invention having a pair of moisture sensor units obtained in the above examples can function as a moisture sensor for the direct detection of water vapor in an atmosphere, the operation mechanism of which is as follows: As mentioned above, this sensor is a thermal conduction type moisture sensor which is composed of a pair of moisture sensor units and which utilizes the phenomenon that the thermal conductivity of the atmosphere, the water vapor of which is to be detected, varies depending upon the amount of water vapor. One of the sensor units, a first sensor unit, is exposed to the atmosphere to be measured so that a variation in the amount of water vapor of the atmosphere to be detected is transmitted as a variation in thermal conductivity of the atmosphere to the said sensor unit. The other of the sensor units, a second sensor unit, is sealed within a container containing dry nitrogen gas, etc., therein so that the sensor unit (especially, the sensitive film) does not come into contact with water vapor from the outside of the container. Then, both the sensor units are heated to the same temperature. Provided that the amount of water vapor of the atmosphere to be detected is maintained at a fixed value, when the temperature of the atmosphere varies, the temperatures of both the first and second sensor units vary to the same extend. However, in fact, the variation in the thermal conductivity of the environment in which the first sensor unit is located is different from that of the thermal conductivity of the environment in which the second sensor unit is located, depending upon the amount of water vapor of each of the said environments. Accordingly, the variation in the temperature of the first sensor unit is different in extent from that of the temperature of the second sensor unit. Moreover, the effect of the temperature of the environment for the first sensor unit on the first sensor unit is the same as that of the temperature of the environment for the first sensor unit on the second sensor unit, so that the difference in the temperature variation between the first and second sensor units depends upon the amount of water vapor of the atmosphere, and thus the amount of water vapor can be detected from the difference in output of the two sensor units. The output signals from the sensor units can be obtained by a variation in the electrical resistance of the sensitive films based on the temperature variation in the sensor units.

Figure 4:
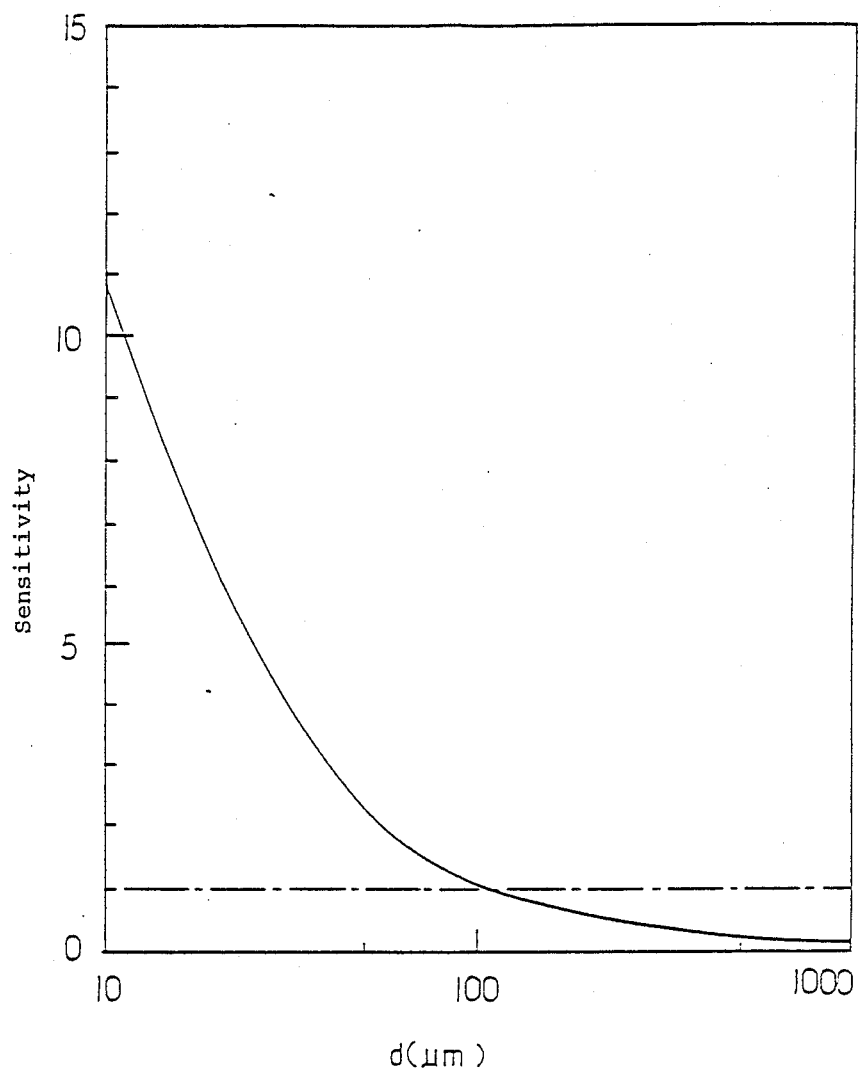
FIG. 4 is a curve showing the moisture-sensitivity characteristics of a moisture sensor of this invention.

Since the sensor of this invention works based on the above-mentioned operation mechanism, the sensitive film must be formed on a substrate which has excellent heat-insulation in order to have the sensor attain high sensitivity, quick response and a lowered power consumption. For this reason, the heat capacity of the sensor must be minimized, and moreover the sensitive film must be made of a material having a large thermistor constant. For these purposes, a fine processing technique such as a micro-machining technique, photolithography, etc., is used so that the sensor of this example can be provided with a structure having lowered heat-capacity which is not attainable by conventional sensor structures. Moreover, a thin film made of Ge, SiC, etc., having the same thermistor constant as thermistors used for low temperatures that are commonly available is used as a sensitive film material, so that a surprising improvement in detection sensitivity, response speed and reduced power consumption can be achieved. FIG. 4 shows a characteristic curve (a solid line) illustrating the relationship between the sensitivity and the thickness of the microbridge with regard to an absolute-moisture sensor having a microbridge structure in which the sensitive film is made of Ge. The sensitivity is represented by A/B, wherein A is the ratio of the resistance variation in the first sensor unit to that of the second sensor unit in the environment containing a give humidity, and B is the ratio of the resistance variation in one of the sensor units constituting a conventional thermal conduction type absolute-moisture sensor to that of the other sensor unit thereof in the environment under the same conditions as the above-mentioned. The characteristic curve of a conventional moisture sensor is indicated by a dotted line. FIG. 4 indicates that the heat capacity of the sensor of this example is lowered with a decrease in the thickness of the microbridge, and that the sensitivity of the sensor of this example is more than ten times that of a conventional sensor when the thickness of the microbridge, d is b 10 μm.

As mentioned above, the moisture sensor of this example can be used as an absolute-moisture sensor of a thermal conduction type which enables the direct detection of water vapor so that a high detection sensitivity and a quick response can be achieved. Moreover, this sensor detects water vapor by a physical process, so that the detection of water vapor can be carried out with accuracy without any influence of light, heat, oily substances, dust, etc., from the outside on the sensor. Thus, this sensor is applicable to a microwave oven sensor by which the degree of doneness of the food can be determined.

Example 3

FIGS. 5a to 5c show another moisture sensor of this invention, which has a diaphragm structure. It is manufactured as follows: Thin insulating layers 2 and 21 are formed on the upper surface and the bottom surface of a Si-substrate 1, respectively. Such thin insulating layers are also formed on the side faces of the Si-substrate 1. The insulating layer 21 is subjected to an etching treatment to form a given shaped and sized mask for the succeeding anisotropic etching process. Then, the Si substrate 1 is subjected to an anisotropic etching treatment to remove the center area in the bottom of the Si substrate 1 which is not coated with the insulating layer 21, resulting in a double-layered diaphragm portion 7 which is composed of a part of the insulating layer 2 covering the upper surface of the Si substrate 1 and the central thin portion of the Si substrate 1. On the diaphragm portion 7, a sensitive film 4 which has been patterned with a given shape and size is disposed. Then, comb-shaped electrodes 5 are connected to the sensitive film 4, resulting in a moisture sensor unit.

A dopant such as boron, etc., is diffused, in advance, into the portion of the Si substrate 1 corresponding to the diaphragm portion 7. This boron-doped portion of the Si substrate functions as an etching shielding layer in the anistropic etching process. Accordingly, the resulting diaphragm portion 7 is composed of the boron-doped portion of the Si substrate 1 and the insulating layer 2. The thickness of the Si substrate 1 corresponding to the diaphragm portion 7 is controlled by the regulation of the diffusion of a dopant such as boron, etc., into the Si substrate 1, but it is also possible by the regulation of the length of the anisotropic etching process. The portion of the Si substrate 1 corresponding to the diaphragm portion 7 can be, of course, removed completely by the etching treatment to form a mono-layered diaphragm portion constituted by the insulating layer 2 alone. In this case, a dopant is not used.

In this way, a moisture sensor having a diaphragm structure with a surprisingly lowered heat capacity that cannot be created by conventional thermal conduction type moisture sensors is obtained. Although the response characteristics of this sensor are slightly inferior to those of the other sensors with a bridge or cantilever structure of this invention, since the diaphragm structure is superior to the bridge and cantilever structures in mechanical strength, this diaphragm type sensor can be preferably used under severe conditions where high sensitivity, quick response, reduced power consumption and sufficient mechanical strength are required.

Example 4

FIG. 6 shows another moisture sensor with a diaphragm structure of this invention, in which a first sensor unit (i.e., a detecting sensor unit) 8 is positioned onto a second sensor unit (i.e., a reference sensor unit) in such a manner that the sensitive film section of the reference sensor unit 9 is located within the diaphragm portion of the detecting sensor unit 8 so as to form an air-tight system therebetween, so that the atmosphere around the sensitive film section of the reference sensor unit 9 can be sealed within a hollow formed between the detecting and reference sensor units 8 and 9. Thus, the detecting and reference sensor units 8 and 9 are incorporated into one body, resulting in an absolute-moisture sensor chip. The above-mentioned structure of the moisture sensor enables the miniaturization of the chip of the sensor. A joining process for uniting the sensor units 8 and 9 into one body can be carried out by a batch treatment for each wafer. Moreover, this joining process by which the sensitive film section of the reference sensor unit 9 is sealed within the hollow formed between the detecting and reference sensor units 8 and 9 is simplified as compared with a process in which the sensitive film section is sealed by the use of a separate part such as a container housing. The joining process does not require such a separate part, so that the moisture sensor of this example can be obtained at a reduced cost. The sensor units constituting the sensor of this example are manufactured in the same way as those of the sensor of each of the above-mentioned examples, except for the following: In the manufacture of the detecting sensor unit 8, the Si substrate is subjected to an anisotropic etching treatment to form not only the diaphragm portion 7, but also windows 10 for the pads of the reference sensor unit 9, from which lead wires of the reference sensor unit 9 are drawn. In the manufacture of the reference sensor unit 9, a joining medium is disposed on the surface of the insulating layer 2 of the reference sensor unit 9, on which the sensitive film 4 is formed, by the sputtering method, vacuum vapor deposition, chemical vapor deposition or the like, followed by subjection to an etching treatment to remove the portion of the joining medium which is not required for the connection of the reference sensor unit 9 to the detecting sensor unit 8, resulting in a patterned joining medium 11. With the patterning process of the joining medium, alternatively, the portion of the insulating layer 2 which is not required for the connection of the reference sensor unit 9 to the detecting sensor unit 8 is masked by a resist or the like and then the joining medium is disposed on the insulating layer 2, after which the masking material is removed, resulting in a patterned joining medium 11. It is also possible for the joining medium to be disposed on the entire area of the insulating layer 2 and then the portions of the joining medium alone corresponding to the pad portions of the reference sensor unit 9 are removed. The joining medium 11 is a thin film which is made of a relatively low melting point material such as glass with a low melting point, PbO, etc.

The resulting detecting sensor unit wafer is placed onto the resulting reference sensor unit wafer so that they face each other. They are fixed to each other by a fixing means and sintered at a given temperature for a given period in a dilute gas atmosphere such as $N_2$, Ar, etc., resulting in a united hollow structure which encloses the dilute gas therein. Then, the united body composed of the two wafers is diced to form an absolute-moisture sensor chip. The moisture sensor obtained in this example is a supercompact and miniaturized absolute-moisture sensor. Moreover, only a small number of sensor parts are used and the production process is simplified, so that the production cost can be suprisingly reduced.

Example 5

In order to have the sensor of this invention attain high sensitivity, quick response and minimum power consumption, the production of a sensor with lowered heat capacity and excellent heat radiation is required. For this purpose, the above-mentioned examples explain sensors with a bridge, cantilever or diaphragm structure.

This example further explains a sensor with a sensitive film having a rough surface or a substrate having a rough surface on which the sensitive film is formed, so that the heat-radiation area of the sensor can be enlarged, thereby attaining excellent heat radiation.

Figure 7A:
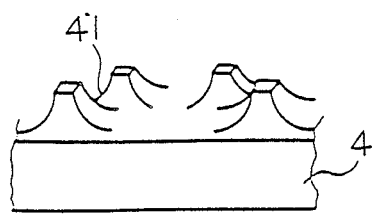
Figure 7B:
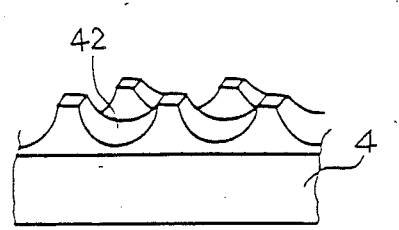
Figure 8A:
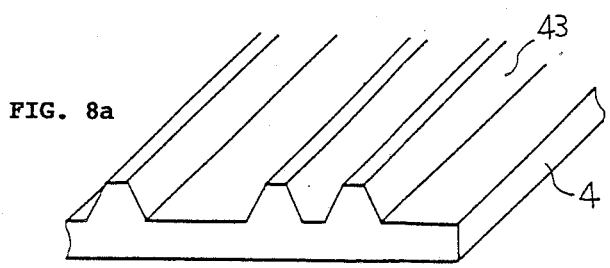
Figure 8B:
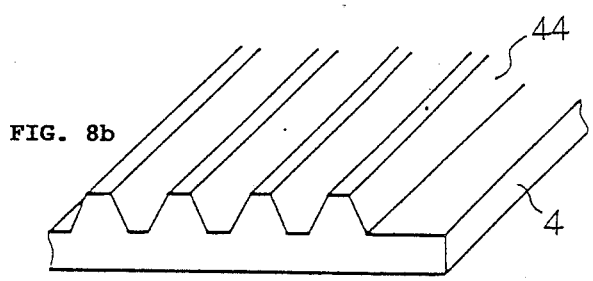
Figure 9:
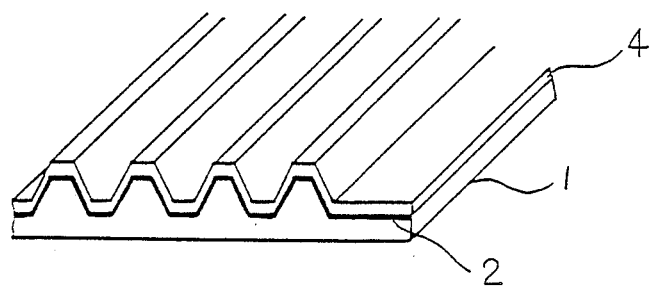
Figure 10:
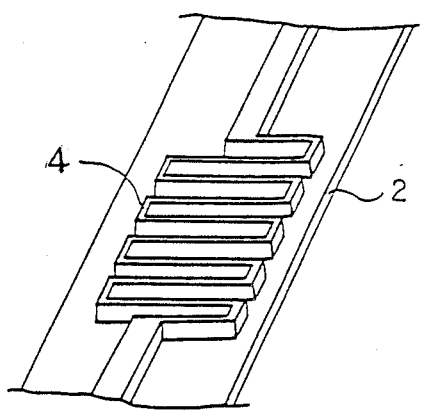
FIG. 10 is a perspective view showing the meandering-shaped sensitive film of this invention.
Figure 11A:
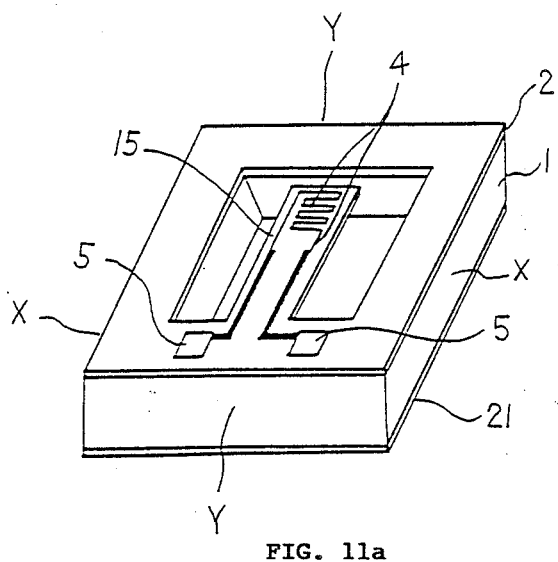
FIG. 11a is a perspective view showing a cantilever type sensor unit of this invention.
Figure 11B:
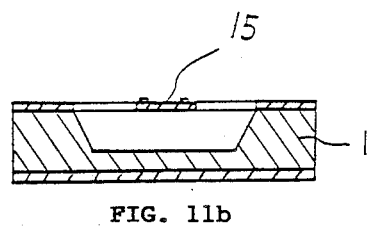
Figure 11C:
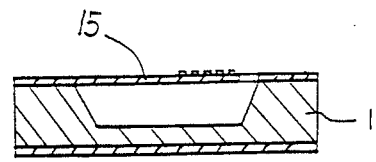
Figure 12:
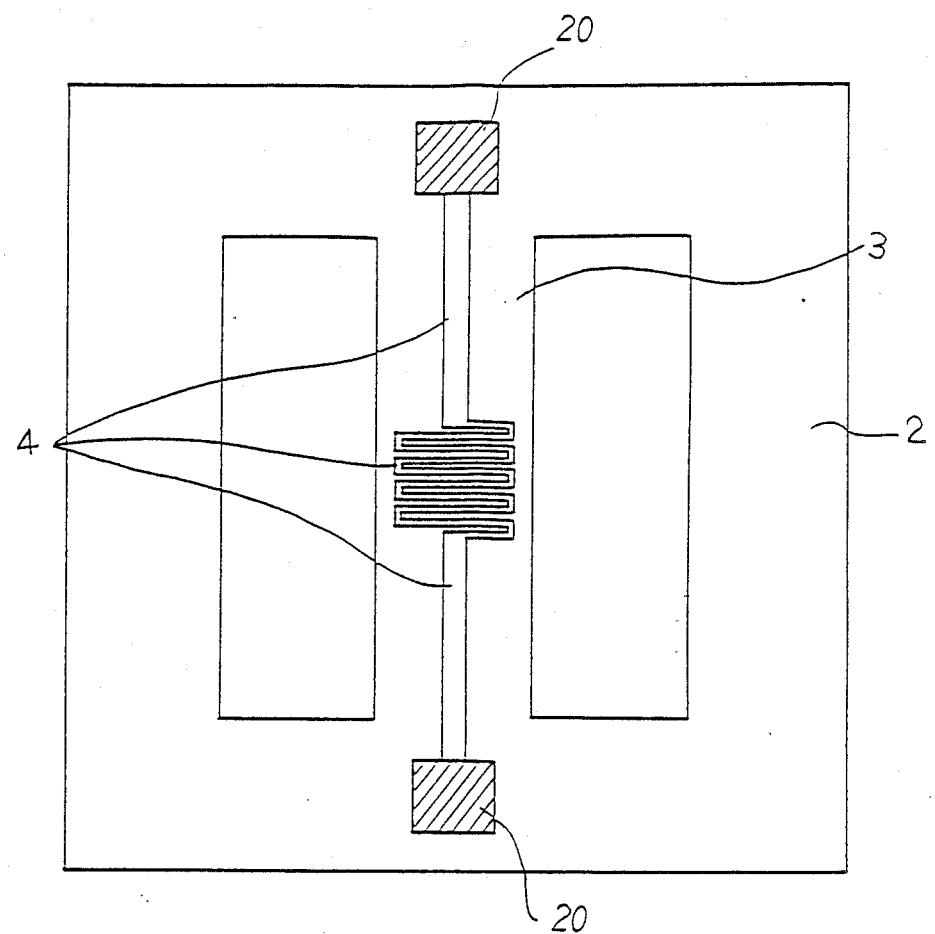
FIG. 12 is a plane view showing a bridge type sensor unit of this invention having a meandering shaped sensitive film.

Each sensor unit constituting the above-mentioned sensor is manufactured in the same way as that of Example 1 except for the formation of the sensitive film 4. The sensitive film 4 is formed on the insulating layer 2 by vacuum vapor deposition, the sputtering method, chemical vapor deposition, etc., and subjected to a fine processing treatment to form the desired pattern having a given shape and size, as mentioned in Example 1. Then, the sensitive film 4 is processed by photolithography and a chemical or plasma etching technique so that the surface of the sensitive film 4 can be formed into a wavy pattern as shown in FIGS. 7 to 9. The wavy pattern is composed of a plurality of trapezoidal projections 41 that are irregularly disposed as shown in FIG. 7a, a plurality of pyramidal projections (not shown), a plurality of conical projections (not shown), or a plurality of hemispherical projections (not shown). It can be also made into a wavy pattern 43, as shown in FIG. 8a, each wave of which has a flat top. It can be also made into an irregular pattern 42 or 44 with a uniform pitch as shown in FIGS. 7b or 8b. Instead of the above-mentioned processing of the sensitive film, the surface of the insulating layer 2 or, when the bridge structure is constituted by the substrate portion and the insulating layer 2, the surface of the substrate 1 can be processed and then the sensitive film 4 be disposed thereon, so that the sensitive film 4 can be formed into an irregular pattern with a uniform pitch as shown in FIG. 9. Alternatively, the sensitive film 4 is processed by photolithography and a chemical or physical etching technique to form into a zigzag pattern or a meandering pattern with a given line width and line space, as shown in FIG. 10. FIGS. 11a to 11c show a sensor unit of this invention which has a sensitive film 4 of a meandering pattern on the cantilever 15 formed by a part of the insulating layer 2. In order to form the sensitive film 4 into a meandering pattern, it is also possible to, first, process the surface of the portion of the substrate 1 on which the sensitive film 4 is finally formed, into an irregular pattern and then dispose the sensitive film 4 thereon, resulting in a meandering shaped sensitive film. The sensitive film can be made of materials having a large thermistor constant such as Ge, SiC, TaN, etc. The sensitive film of this example is made of Ge. Thin film electrodes 5 are disposed to be in contact with the sensitive film 4 in the same manner as those of Example 2. When the sensitive film 4 is formed in a meandering pattern, the pad portions 20 positioned so as to be connected to the said sensitive film 4 shown in FIG. 12 are used as electrodes.

Thereafter, the Si substrate is subjected to an anisotropic etching treatment with an etchant such as a solution containing ethylenediamine, pyrocatechol and water, and the etching of the Si crystal proceeds in the direction of the preferential crystal axis in the area of the Si substrate 1 which is not coated with the insulating layer, so that removal of the portion of the Si substrate positioned below the bridged pattern of the insulating layer 2 can be effected, resulting in a chip of moisture sensor units with a microbridge structure in which the irregularity of the surface of the sensitive film makes the heat removal area large.

Example 6

This example provides another moisture sensor unit, which has the same structure as that of Example 3, except that the surface of the sensitive film 4 is made into an irregular pattern by a precision processing technique. The irregular pattern of the sensitive film 4 and the formation thereof are the same as those of the sensitive film of Example 5.

Example 7

This example describes materials for the electrodes of the moisture sensor unit, for example, of Example 1. The electrodes 5, which are made into, for example, a comb-shape, are made of metals having a low thermal conductivity such as titanium, etc., by electron beam vapor deposition, vacuum vapor deposition, the sputtering method or the like.

The thermal conductivity of $SiO_2$, which is a typical insulating layer material, is 1.4 W/M·K and the thermal conductivities of Ag, Cu, Au, and Al, which are typical materials for electrodes formed on the insulating layer, are 428, 403, 319 and 236 W/M·K, respectively. When a low thermal conductivity metal, i.e., titanium or the like (the thermal conductivity thereof being 20 W/M·K) is used as the electrodes of the sensor unit, the heat capacity is reduced thereby making the unit optimal for use in a bridge, cantilever, or diaphragm structure sensor unit of this invention.

The electrical conductivity of a metal is generally proportional to the thermal conductivity of the metal. The electrical conductivity of titanium or the like, the thermal conductivity of which is extremely low, is also extremely low, and accordingly the electrical resistance of electrodes made of titanium or the like is higher than that of the electrodes made of Al or the like. However, since the electrical resistance of a sensitive film made of Ge, etc., is remarkably high, that of titanium or the like is negligible. Moreover, titanium, which has a high melting point, is stable in heat, and the adhesive property of titanium to the insulating layer of SiO or the like is excellent, so that the sensor structure of this example using electrodes of titanium or the like can achieve extreme reliability.

Example 8

Figure 13A:
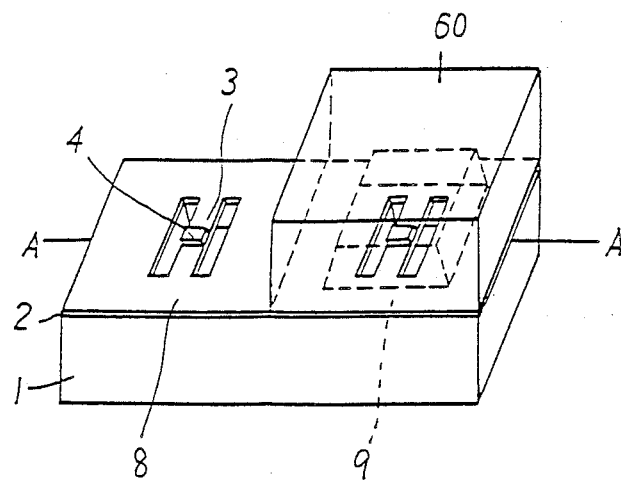
FIG. 13a is a perspective view showing a sensor of this invention in which the substrate of the detecting sensor unit is common to that of the reference sensor unit.
Figure 13B:
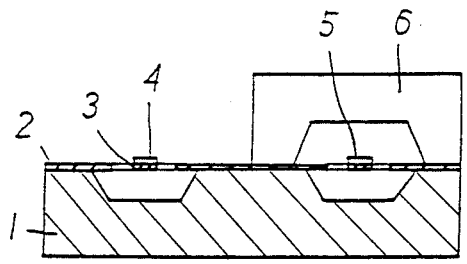

FIGS. 13a and 13b show another sensor of this invention, in which a pair of sensitive films 4 are placed on the same substrate 1. One sensitive film 4 belongs to the detecting sensor unit 8 and the other sensitive film 4 belongs to the reference sensor unit 9. The sensitive film section of the reference sensor unit 9 is sealed within a container 60. The upper surface of the substrate 1 is etched to form a concavity, in advance, in which the container 60 is placed and connected to the substrate 1 by glass with a low melting point or a bonding agent. The bonding of the container 60 to the substrate 1 can be also carried out by an electric field application technique. The production process of this sensor is the same as those of the above-mentioned examples.

Although the substrate and/or the container is made of Si, they can be made of compound semiconductors composed of elements of the III–V groups such as GaAs.

The above-mentioned examples disclose moisture sensors alone, but this invention is, of course, applicable to a variety of sensors such as gas sensors, infrared ray sensors, etc. When the sensor of this invention is used as a gas sensor, if it is sensitive to a specific gas alone, a specific-gas permeable membrane is disposed on the sensitive film and/or in ventilation openings of the housing. A gas selection column used in gas chromatography can also be used. The gas to be enclosed within the container can be selected depending upon the kind of gas to be detected. The container can be, of course, a vacuum.

When goldblack or the like are deposited on the sensitive film by vapor deposition, etc., the resulting sensor can be used as an infrared ray sensor. In the detection of infrared rays, the sensitive film of the said sensor is not heated, which is different from the sensitive film of the above-mentioned moisture sensor. An increase in the temperature of the sensitive film due to the radiation of the infrared rays onto the sensitive film is detected.

Since infrared rays permeate silicon, sensor parts such as a container made of silicon must be coated with an infrared ray-reflecting film.

Moreover, when a plurality of sensitive films are formed on the same substrate, a sensor in which a moisture sensor and a gas sensor are united into one body can be obtained.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A sensor having a pair of sensor units, one of which is a detecting sensor unit and the other of which is a reference sensor unit, wherein said detecting sensor unit comprises a substrate with a hollow portion, a thin insulating layer with a bridge shape disposed on said substrate, a sensitive film disposed on the bridge portion of said thin insulating layer, and a pair of electrodes being in contact with said sensitive film, the sensitive film section being exposed to an atmosphere to be measured so that the electrical resistance of said sensitive film changes with a variation in the physical quantity of said atmosphere to be detected; and said reference sensor unit comprises a substrate having a hollow portion, a thin insulating layer with a bridge shape disposed on said substrate, a sensitive film disposed on the bridge portion of said thin insulating layer, and a pair of electrodes being in contact with said sensitive film, the sensitive film section being sealed within a shielding container so that the electrical resistance of said sensitive film is not influenced by a variation in the physical quantity of the atmosphere outside of said container, whereby the absolute physical quantity of the atmosphere to be detected is determined by the output power of said sensor based on a difference between said electrical resistance of the detecting sensor unit and said electrical resistance of the reference sensor unit.

2. A sensor according to claim 1, wherein the thickness of each said thin insulating layer is 100 $\mu$m or less.

3. A sensor according to claim 1, wherein each said sensitive film is made of a material selected from the group consisting of SiC, TaN, Ge, Si, $BaTiO_3$ or a material mainly containing at least one of these substances.

4. A sensor according to claim 1, wherein the surface of each said sensitive film is formed into an irregular pattern.

5. A sensor according to claim 4, wherein each said sensitive film is made into a meandering pattern.

6. A sensor according to claim 4, wherein the surface of each said sensitive film is formed into an irregular pattern by etching.

7. A sensor according to claim 4, wherein the surface of the underlying layer on which each said sensitive film is disposed is formed into an irregular pattern, so that the surface of the sensitive film disposed on the irregular pattern surface of said underlying layer can be formed into said irregular pattern.

8. A sensor according to claim 1, wherein each said substrate and said container are mainly made of a material selected from
 silicon, and
 a compound semiconductor composed of elements of the III–V groups.

9. A sensor according to claim 1, wherein each pair of said electrodes is made of a metal having a thermal conductivity of 100 W/M·K or less.

10. A sensor according to claim 9, wherein said metal is titanium.

11. A sensor according to claim 1, wherein said detecting sensor unit and said reference sensor unit are separate from each other.

12. A sensor according to claim 1, wherein the substrate of said detecting sensor unit is common to that of said reference sensor unit.

13. A sensor according to claim 12, wherein two or more sensitive films are disposed on said substrate.

14. A sensor according to claim 1, wherein said physical quantity to be detected is selected from the group consisting of water vapor, gas and infrared rays.

15. A sensor having a pair of sensor units, one of which is a detecting sensor unit and the other of which is a reference sensor unit, wherein said detecting sensor unit comprises a substrate with a hollow portion, a thin insulating layer with a diaphragm disposed on said substrate, a sensitive film disposed on the diaphragm portion of said thin insulating layer, and a pair of electrodes being in contact with said sensitive film, the sensitive film section being exposed to an atmosphere to be measured so that the electrical resistance of said sensitive film changes with a variation in the physical quantity of said atmosphere to be detected; and said reference sensor unit comprises a substrate having a hollow portion, a thin insulating layer with a diaphragm disposed on said substrate, a sensitive film disposed on the diaphragm portion of said thin insulating layer, and a pair of electrodes being in contact with said sensitive film, the sensitive film section being sealed within a shielding container so that the electrical resistance of said sensitive film is not influenced by a variation in the physical quantity of the atmosphere outside of said container, whereby the absolute physical quantity of the atmosphere to be detected is determined by the output power of said sensor based on a difference between said electrical resistance of the detecting sensor unit and said electrical resistance of the reference sensor unit.

16. A sensor according to claim 15, wherein said detecting sensor unit and said reference sensor unit are united into one body by depositing said detecting sensor unit on said reference sensor unit in such a manner that the sensitive film section of said reference sensor unit is sealed within the hollow portion of said detecting sensor unit.

17. A sensor having a pair of sensor units, one of which is a detecting sensor unit and the other of which is a reference sensor unit, wherein said detecting sensor unit comprises a substrate with a hollow portion, a thin insulating layer with a bridge disposed on said substrate, a sensitive film disposed on the bridge portion of said thin insulating layer, and a pair of electrodes being in contact with said sensitive film, the sensitive film section being exposed to an atmosphere to be measured so that the electrical resistance of said sensitive film changes with a variation in the physical quantity of said atmosphere to be detected; and said reference sensor unit comprises a substrate having a hollow portion, a thin insulating layer with a diaphragm disposed on said substrate, a sensitive film disposed on the diaphragm portion of said thin insulating layer, and a pair of electrodes being in contact with said sensitive film, the sensitive film section being sealed within a shielding container so that the electrical resistance of said sensitive film is not influenced by a variation in the physical quantity of the atmosphere outside of said container, whereby the absolute physical quantity of the atmosphere to be detected is determined by the output power of said sensor based on a difference between said electrical resistance of the detecting sensor unit and said electrical resistance of the reference sensor unit.

18. A sensor having a pair of sensor units, one of which is a detecting sensor unit and the other of which is a reference sensor unit, wherein said detecting sensor unit comprises a substrate with a hollow portion, a thin insulating layer with a diaphragm disposed on said substrate, a sensitive film disposed on the diaphragm portion of said thin insulating layer, and a pair of electrodes being in contact with said sensitive film, the sensitive film section being exposed to an atmosphere to be measured so that the electrical resistance of said sensitive film changes with a variation in the physical quantity of said atmosphere to be detected; and said reference sensor unit comprises a substrate having a hollow portion, a thin insulating layer with a bridge shape disposed on said substrate, a sensitive film disposed on the bridge portion of said thin insulating layer, and a pair of electrodes being in contact with said sensitive film, the sensitive film section being sealed within a shielding container so that the electrical resistance of said sensitive film is not influenced by a variation in the physical quantity of the atmosphere outside of said container, whereby the absolute physical quantity of the atmosphere to be detected is determined by the output power of said sensor based on a difference between said electrical resistance of the detecting sensor unit and said electrical resistance of the reference sensor unit.

19. A sensor having a pair of sensor units, one of which is a detecting sensor unit and the other of which is a reference sensor unit, wherein said detecting sensor unit comprises a substrate with a hollow portion, a thin insulating layer with a cantilever shape disposed on said substrate, a sensitive film disposed on the cantilever portion of said thin insulating layer, and a pair of electrodes being in contact with said sensitive film, the sensitive film section being exposed to an atmosphere to be measured so that the electrical resistance of said sensitive film changes with a variation in the physical quantity of said atmosphere to be detected; and said reference sensor unit comprises a substrate having a hollow portion, a thin insulating layer with a cantilever shape disposed on said substrate, a sensitive film disposed on the cantilever portion of said thin insulating layer, and a pair of electrodes being in contact with said sensitive film, the sensitive film section being sealed within a shielding container so that the electrical resistance of said sensitive film is not influenced by a variation in the physical quantity of the atmosphere outside of said container, whereby the absolute physical quantity of the atmosphere to be detected is determined by the output power of said sensor based on a difference between said electrical resistance of the detecting sensor unit and said electrical resistance of the reference sensor unit.

20. A sensor having a pair of sensor units, one of which is a detecting sensor unit and the other of which is a reference sensor unit, wherein said detecting sensor unit comprises a substrate with a hollow portion, a thin insulating layer with a cantilever disposed on said substrate, a sensitive film disposed on the cantilever portion of said thin insulating layer, and a pair of electrodes being in contact with said sensitive film, the sensitive film section being exposed to an atmosphere to be measured so that the electrical resistance of said sensitive film changes with a variation in the physical quantity of said atmosphere to be detected; and said reference sensor unit comprises a substrate having a hollow portion, a thin insulating layer with a diaphragm disposed on said substrate, a sensitive film disposed on the diaphragm portion of said thin insulating layer, and a pair of electrodes being in contact with said sensitive film, the sensitive film section being sealed within a shielding container so that the electrical resistance of said sensitive film is not influenced by a variation in the physical quantity of the atmosphere outside of said container, whereby the absolute physical quantity of the atmosphere to be detected is determined by the output power of said sensor based on a difference between said electrical resistance of the detecting sensor unit and said electrical resistance of the reference sensor unit.

21. A sensor having a pair of sensor units, one of which is a detecting sensor unit and the other of which is a reference sensor unit, wherein said detecting sensor unit comprises a substrate with a hollow portion, a thin insulating layer with a diaphragm disposed on said substrate, a sensitive film disposed on the diaphragm portion of said thin insulating layer, and a pair of electrodes being in contact with said sensitive film, the sensitive film section being exposed to an atmosphere to be measured so that the electrical resistance of said sensitive film changes with a variation in the physical quantity of said atmosphere to be detected; and said reference sensor unit comprises a substrate having a hollow portion, a thin insulating layer with a cantilever shape disposed on said substrate, a sensitive film disposed on the cantilever portion of said thin insulating layer, and a pair of electrodes being in contact with said sensitive film, the sensitive film section being sealed within a shielding container so that the electrical resistance of said sensitive film is not influenced by a variation in the physical quantity of the atmosphere outside of said container, whereby the absolute physical quantity of the atmosphere to be detected is determined by the output power of said sensor based on a difference between said electrical resistance of the detecting sensor unit and said electrical resistance of the reference sensor unit.

22. A sensor having a pair of sensor units, one of which is a detecting sensor unit and the other of which is a reference sensor unit, wherein said detecting sensor unit comprises a substrate with a hollow portion, a thin insulating layer with a cantilever shape disposed on said substrate, a sensitive film disposed on the cantilever portion of said thin insulating layer, and a pair of electrodes being in contact with said sensitive film, the sensitive film section being exposed to an atmosphere to be measured so that the electrical resistance of said sensitive film changes with a variation in the physical quantity of said atmosphere to be detected; and said reference sensor unit comprises a substrate having a hollow portion, a thin insulating layer with a bridge shape disposed on said substrate, a sensitive film disposed on the bridge portion of said thin insulating layer, and a pair of electrodes being in contact with said sensitive film, the sensitive film section being sealed within a shielding container so that the electrical resistance of said sensitive film is not influenced by a variation in the physical quantity of the atmosphere outside of said container, whereby the absolute physical quantity of the atmosphere to be detected is determined by the output power of said sensor based on a difference between said electrical resistance of the detecting sensor unit and said electrical resistance of the reference sensor unit.

23. A sensor having a pair of sensor units, one of which is a detecting sensor unit and the other of which is a reference sensor unit, wherein said detecting sensor unit comprises a substrate with a hollow portion, a thin insulating layer with a bridge shape disposed on said substrate, a sensitive film disposed on the bridge portion of said thin insulating layer, and a pair of electrodes being in contact with said sensitive film, the sensitive film section being exposed to an atmosphere to be measured so that the electrical resistance of said sensitive film changes with a variation in the physical quantity of said atmosphere to be detected; and said reference sensor unit comprises a substrate having a hollow portion, a thin insulating layer with a cantilever shape disposed on said substrate, a sensitive film disposed on the cantilever portion of said thin insulating layer, and a pair of electrodes being in contact with said sensitive film, the sensitive film section being sealed within a shielding container so that the electrical resistance of said sensitive film is not influenced by a variation in the physical quantity of the atmosphere outside of said container, whereby the absolute physical quantity of the atmosphere to be detected is determined by the output power of said sensor based on a difference between said electrical resistance of the detecting sensor unit and said electrical resistance of the reference sensor unit.

* * * * *